United States Patent [19]

Hoehn, Jr.

[11] Patent Number: 4,591,785

[45] Date of Patent: May 27, 1986

[54] METHOD FOR DETECTING SOFT SPOTS IN THE HARDNESS OF STEEL CASING

[75] Inventor: Gustave L. Hoehn, Jr., Dallas, Tex.

[73] Assignee: Mobil Oil Corporation, New York, N.Y.

[21] Appl. No.: 545,332

[22] Filed: Oct. 25, 1983

[51] Int. Cl.$^4$ .................. G01N 27/80; G01N 27/82; G01R 33/12

[52] U.S. Cl. .................. 324/239; 324/220; 324/240

[58] Field of Search ............... 324/234, 235, 238–240, 324/228, 220, 221, 222, 241–243

[56] References Cited

U.S. PATENT DOCUMENTS

| 2,797,386 | 6/1957 | Callan | 324/229 X |
|---|---|---|---|
| 2,896,155 | 7/1959 | Cook | 324/220 X |
| 2,945,176 | 7/1960 | Irwin | 324/227 |
| 2,952,806 | 9/1960 | Safferling | 324/239 |
| 3,265,964 | 8/1966 | Hunsaker | 324/239 X |
| 3,273,054 | 9/1966 | Cook | 324/220 |
| 3,432,747 | 3/1969 | Quittner | 324/239 |
| 3,434,048 | 3/1969 | Law et al. | 324/239 |
| 3,597,678 | 8/1971 | Fearon | 324/220 |
| 4,468,619 | 8/1984 | Reeves | 324/220 |
| 4,481,470 | 11/1984 | Wallace | 324/228 |

Primary Examiner—Gerard R. Strecker
Attorney, Agent, or Firm—A. J. McKillop; Michael G. Gilman; George W. Hager, Jr.

[57] ABSTRACT

A method of measuring hardness in steel casing to detect soft spots. A magnetizing force is generated and traversed along the length of the steel casing. A flux density is created along those portions of the steel casing traversed by the magnetizing force. The flux density is monitored to detect any change in such flux density caused by the presence of a soft spot in the hardness of the steel casing.

5 Claims, 2 Drawing Figures

FIG. 2
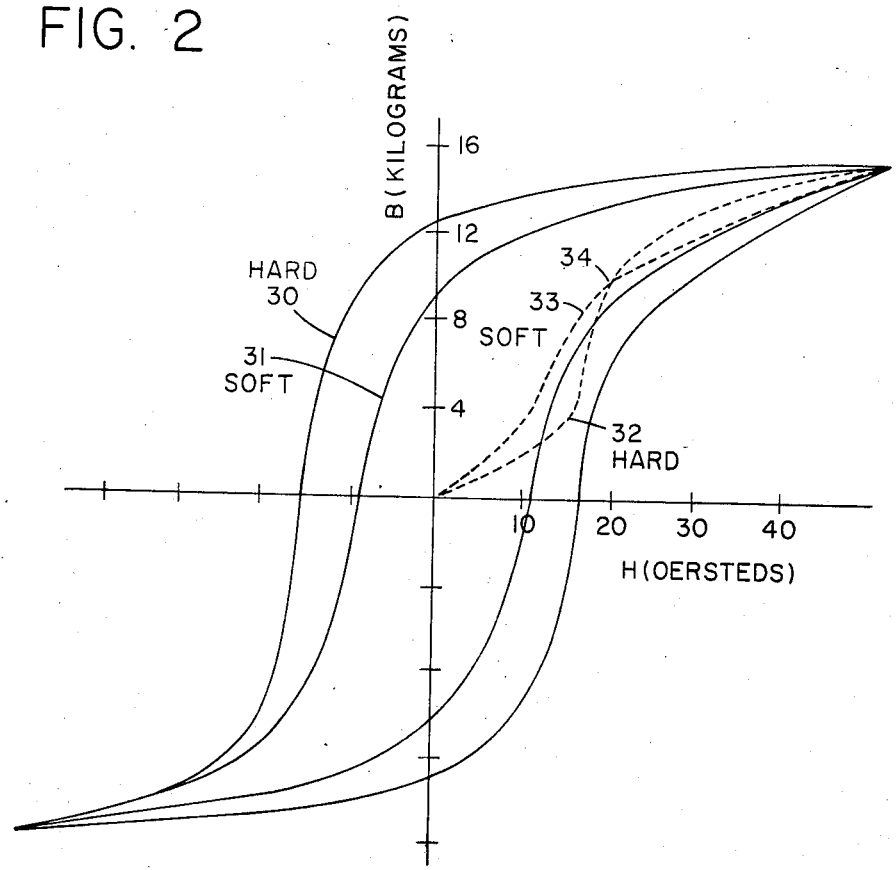
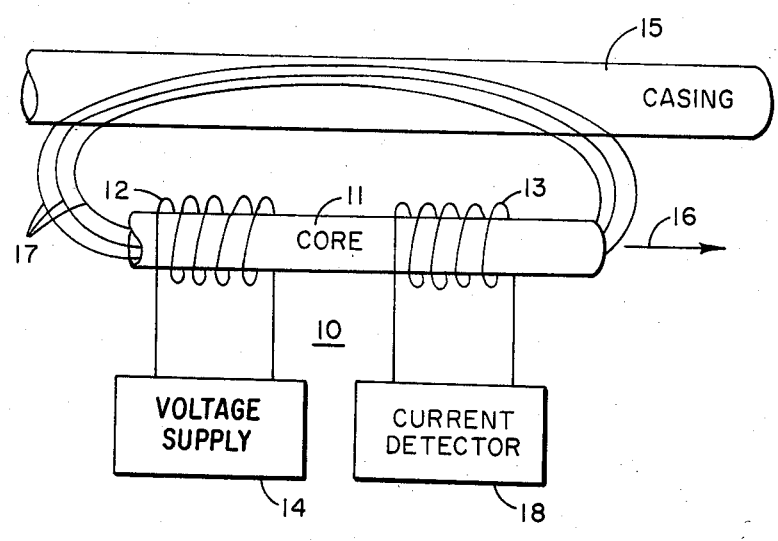
FIG. 1

METHOD FOR DETECTING SOFT SPOTS IN THE HARDNESS OF STEEL CASING

BACKGROUND OF THE INVENTION

Failures in steel casing, or piping, due to improper heat treatment has long been a problem in well completion. Improperly heat treated casing if placed in service in a borehole will be subject to failure because borehole pressures are too high for the inferior hardness properties of the improperly heat treated casing. Casing may be improperly heat treated in its entirety or in one or more areas along the length of the casing. The minimum length will vary from manufacturer to manufacturer because of the differences in heat treating equipment, but will be about six inches.

Any non-destructive test of such a casing before being set in the well is at best an indirect test. For example, Brinell hardness testers have been used to impart a blow at a certain point on the surface of the casing with a known force and the degree of penetration into the surface is measured. The hardness of the steel at the surface is presumed to be an indication of the hardness of the steel throughout its thickness at that point.

SUMMARY OF THE INVENTION

The present invention is directed to a method for measuring hardness in steel casing to detect soft spots. A magnetizing force is generated and traversed along the length of the steel casing. The magnetic properties along the length of the steel casing under the influence of the magnetizing force is measured to detect changes in such magnetic properties due to any soft spots in the hardness of said steel casing.

More particularly, a hardness detector employs a steel core surrounded by a magnetizing coil and a detecting coil. A current is passed through the magnetizing coil to create the magnetizing force. The detector is passed along the length of the steel casing that is to be hardness tested to create a flux flow through the steel core and the steel casing. The current induced in the detecting coil in response to the flux flow through the steel core is detected as a measure of the hardness of that portion of the steel casing subjected to the magnetizing force.

BRIEF DESCRIPTION OF THE DRAWINGS

FIG. 1 is a pictorial representation of the steel casing hardness detector of the present invention.

FIG. 2 illustrates hysteresis curves of hard and soft steels useful in carrying out the hardness detection method of the present invention.

DESCRIPTION OF THE PREFERRED EMBODIMENTS

It is a generally known principle that there is a good correlation between hardness and magnetic properties of steel. It is a specific aspect of the present invention to apply this principle in a method for testing for soft spots in the hardness of steel tubing, such as well casing, prior to its being used under high pressure conditions as is found at several thousand feet of borehole depth when producing an oil or gas well.

Referring to FIG. 1, a hardness detector includes the core 11, the magnetizing coil 12, and the detecting coil 13. Magnetic lines of flux are imparted to the core 11 by the passage of current from the voltage supply 14 through the magnetizing coil 12. Detector 10 may be advanced along the steel casing 15 as shown by the path 16 in such a manner that the lines of flux 17 emanating from the core 11 intercept the casing 15. Upon passing through the casing these lines of magnetic flux return to the core as indicated by the directional arrow heads on the lines of magnetic flux. These return flux lines induce an emf in the detecting coil 13. The resulting current flow in coil 13 is measured by the current detector 18. Should the hardness detector 10 pass by a soft spot in the steel casing, there will be a detectable change in the magnitude of the flux density. A change in the flux density causes a change in the emf, and resulting current flow, through coil 13, which is measurable by the current detector 18. Such emf and current flow in coil 13 is proportional to the time rate of change of the magnetic flux in the steel casing.

Not only may soft spots in steel casing be detected by advancing the detector along the outside of the casing, such soft spots may also be detected by passing the detector through the inside of the casing. This is especially true when detecting for soft spots after such casing has been set in a borehole for well production operation.

The nature of the magnetization on hard and soft steels is illustrated in FIG. 2. The outer B-H hysteresis loop 30 is for a ring sample of a 2¾ inch steel casing of P-105 hard steel excited by an alternating magnetizing force or field H, while the inner B-H hysteresis loop 30 is for a ring sample of a 2¾ inch steel casing of J-55 soft steel. It can be seen that both the hard and soft steels saturate at a flux density of about 15 kilogauss. Consequently, the saturation current flow through the detecting coil 13 of FIG. 1 would be the same for both the soft steels even though the hysteresis loops are of different shape. Consequently, if a current flow large enough to saturate the two steels is passed through the magnetizing coil 12, the current detector 18 will not distinguish the difference in magnetic properties of such steels. Further, when the magnetizing force is initially applied to the steels, the hysteresis loops begin at zero and follow the curves 32 for the hard steel (P-105) and 33 for the soft steel (J-55). The initial magnetization for the hard steel is actually below that for the soft steel since it is more difficult to magnetize the hard steel. At point 34, the initial magnetization curves 32 and 33 cross. Above this point 34, the differentials between the two initialization curves, as well as between the loops 30 and 31 become minimized as saturation is approached making it difficult to distinguish between hard and soft steels. More particularly, when both steels approach saturation they produce almost identical responses in detecting coil 13. Even the harmonic content of the detected waveform would be nearly the same with perhaps small phase changes. However, if the driving magnetic field H is held below a level of about ±12 oersteds then the hysteresis loop for soft steel (J-55) would fall along the initialization curve 33 to about 5.4 kilogauss while the hysteresis loop for hard steel (P-105) would fall even further along the initialization curve 32 to about 2.8 kilogauss. In this event, the response in the detecting coil 13 for the soft spots in the steel casing will be greater than for the hard portions and identification of soft spots in steel casing is more readily detectable through amplitude changes in detecting coil 13.

Having now described the method of the present invention in conjunction with the hardness detector 10 of FIG. 1, it should be readily apparent that other types and configurations of hardness detectors may be employed in carrying out the method of the present invention without departing from the spirit and scope of the invention as set forth in the appended claims. For example, the hardness detector may be passed through the steel casing or may be configured so the magnetizing and detecting coils surround the steel casing while passing along its length.

I claim:

1. In a method for detecting soft spots in the hardness of steel casing in which a magnetizing force is traversed along the length of the steel casing to create a flux density along the steel casing as it is traversed by the magnetizing force, and in which the flux density induced in the steel casing is measured to detect any change in the flux density caused by the presence of a soft spot in the hardness of the steel casing, the improvement comprising:
    (a) limiting said magnetizing force to maintain said flux density in the steel casing below the point of flux density intersection along the initial magnetization curves for hard and soft steels so as to maintain a continuing flux density that is greater for the soft spots in said steel casing than for the hard spots, and
    (b) identifying a soft spot in said steel casing when there is an increase in said measured flux density.

2. The method of claim 1 wherein said magnetizing force is selected to maximize the differential in the flux densities along the initial magnetization curves for hard and soft steels below said point of flux density intersection.

3. The method of claim 2 wherein said magnetizing force is maintained at no greater than 20 L oersteds.

4. The method of claim 3 wherein said magnetizing force is maintained at about 12 oersteds.

5. A method for detecting soft spots in the hardness of steel casing, comprising the steps of:
    (a) surrounding a steel core with a magnetizing coil and a detecting coil,
    (b) initially applying a current through said magnetizing coil to create an initial magnetizing force which induces a flux density in said steel casing that maximizes the differentials in the initial magnetization curves of soft spots and hard spots in said steel casing below the point of flux density intersection along said initial magnetization curves for soft and hard steels,
    (c) continuing the application of said current through said magnetizing coil and traversing said steel casing along its length with said steel core to induce a continuing magnetic flux through said steel casing,
    (d) monitoring the current induced in said detecting coil in response to the magnetic flux through said steel casing, the amount of said current flowing through said detecting coil being increased in amplitude when a soft spot of said steel casing is subjected to said continuing magnetic flux, and
    (e) identifying a soft spot in said steel casing in response to an increase in the amplitude of current flowing through said detecting coil.

* * * * *